United States Patent [19]

Shimada et al.

[11] Patent Number: 4,567,164

[45] Date of Patent: Jan. 28, 1986

[54] PHARMACEUTICAL COMPOSITION FOR TREATING PROTOZOAN DISEASE CONTAINING AT LEAST ONE TETROCARCIN

[75] Inventors: Kenjiro Shimada; Masao Otomo, both of Tsuchiura; Fusao Tomita, Machida; Shingo Ito, Tsuchiura, all of Japan

[73] Assignee: Kyowa Hakko Kogyo Co., Ltd., Tokyo, Japan

[21] Appl. No.: 583,695

[22] Filed: Feb. 27, 1984

[30] Foreign Application Priority Data

Mar. 4, 1983 [JP] Japan ................................ 58-35563

[51] Int. Cl.$^4$ ............................................. A61K 31/71
[52] U.S. Cl. .................................... 514/33; 536/16.8; 536/18.1

[58] Field of Search ............................. 536/16.8, 18.1; 424/180; 514/33

[56] References Cited

U.S. PATENT DOCUMENTS 4,346,075  8/1982  Tomita et al. ...................... 536/16.8

OTHER PUBLICATIONS

Chemical Abstracts, vol. 97, p. 537, 1982, No. 143128m.
Chemical Abstracts, vol. 97, 1982, No. 180139m.

Primary Examiner—Johnnie R. Brown
Assistant Examiner—Elli Peselev
Attorney, Agent, or Firm—Antonelli, Terry & Wands

[57] ABSTRACT

Tetrocarcins have remarkable and anti-piroplasma activity and anti-malaria activity, and especially useful for preventing or curing piroplasma disease of cattle.

5 Claims, No Drawings

PHARMACEUTICAL COMPOSITION FOR TREATING PROTOZOAN DISEASE CONTAINING AT LEAST ONE TETROCARCIN

BACKGROUND OF THE INVENTION

This invention relates to a composition for preventing and curing protozoan disease, more specifically piroplasma disease and malaria, which comprises at least one of tetrocarcins and salts thereof and at least one pharmaceutical adjuvant or carrier.

The piroplasma disease is a protozoan disease caused by piroplasma in a broad sense, which includes protozoa of Babesia and Theileria families, and an acute or chronic disease transmitted by mites with the main symptoms of pyrexia, anemia, jaundice, and hemoglobin-uria. Various attempts have been made long for its curing, but its defense is very difficult. It has frequently occurred in many places in the world, and the economic loss is great. On the other hand, in Japan, it has frequently occurred with grazing cattle and also it recently tends to increase with housing cattle, which give rise to problems.

Chemicals against it include 8-aminoquinoline derivatives, etc., but recently many chemical-resistant strains have appeared, and now such chemicals have almost no more practical significance in view of their effect and toxicity, etc.

As the result of extensive studies of effective anti-piroplasma agents against Babesia rodhaini living on small animals (which will be hereinafter referred to as BR), it has been found that tetrocarcins have a strong anti-piroplasma activity and the present invention have been established. Furthermore, when splenectomized cattle were infected with *Theileria sergenti* (which will be hereinafter referred to as TS) (including chemical-resistant strains) to confirm their anti-piroplasma activity, a very strong activity has been found, and their practical significance has been clarified.

DETAILED DESCRIPTION OF THE INVENTION

Tetrocarcins are known to have an anti-bacterial activity against gram-positive and gram-negative bacteria and antitumor activity, and have the following structures:

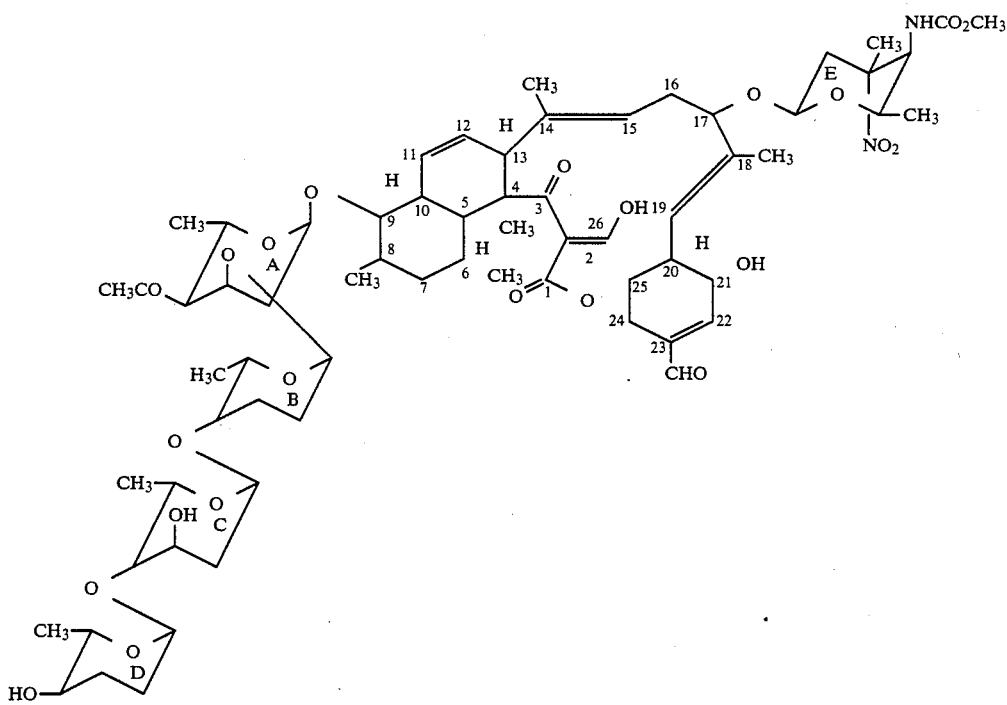

Tetrocarcin A: the above compound
Tetrocarcin B: H in place of sugar D
Tetrocarcin F: H in place of sugars C and D
Tetrocarcin $E_1$: H in place of sugars B to D
Tetrocarcin $E_2$: acetyl in place of sugars B to D, and HO— in place of

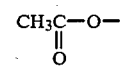

in the A ring
Tetrocarcin F-1: H in place of sugars A to D
Tetrocarcin F-2: H in place of sugars A to D, and H in place of sugar E
Tetrocarcin G: $CH_2OH$ in place of CHO at the 23 position
Tetrocarcin H: $CO_2H$ in place of CHO at the 23 position Furthermore, tetrocarcins C, D, I, J, K, L, M, etc. have the similar structures in addition to the above compounds.

Furthermore, the tetrocarcins include the compounds having an acyl group at position 21 (monoacylates), the compounds having acyl groups at positions 9 and 21 (diacylates), and the compounds having acyl groups at position 9, 17, and 21 (triacylates). The monoacylates, diacylates and triacylates include 21-O-acetyltetrocarcin F-1, 9,21-O-diacetyltetrocarcin F-1, 9,17,21-O-triacetyl-tetrocarcin F-2, etc.

Salts of tetrocarcins includes alkali metal salts such as sodium salt, potassium salt and lithium salt, alkaline earth metal salts such as calcium salt and barium salt, and so on.

Patent applications for these tetrocarcins are given below, some of which have such titles of invention as DC-11, for example DC-11-A, DC-11-B, etc. in place of the title "tetrocarcin":

For tetrocarcin A: Japanese published unexamined patent application No. 138501/1979 (Japanese published examined patent application No. 38159/1981), Japanese published unexamined patent application Nos. 79322/1980 and 139500/1981, and U.S. Pat. No. 4,346,075.

For tetrocarcin B: Japanese published unexamined patent application Nos. 1159794/1981 and 122392/1981.

For tetrocarcin C: Japanase published unexamined patent application Nos. 75500/1981 and 122392/1981.

For tetrocarcin D: Japanese published unexamined patent application No. 122392/1981.

For tetrocarcin $E_1$, $E_2$: Japanese published unexamined patent application No. 38796/1982.

For tetrocarcin F, G, H: Japanese published unexamined patent application No. 53498/1982.

For tetrocarcin I, J, K, L, M: Japanese published unexamined patent application No. 171997/1982.

For tetrocarcin F-1, F-2: Japanse published unexamined patent application No. 7479/1982.

For monoacylate, diacylate and triacylate: Japanese published unexamined patent application No. 7479/1982.

For salts of tetrocarcin: Japanese published unexamined patent application No. 139500/1981.

Tetrocarcins and the salts are useful as an antipiroplasma agent for animals, particularly cattle, as described above, and, as a result of further studies, they have been found useful as an anti-malaria agent for men or animals (for example, poultry).

Tetrocarcins and the salts can be orally or parenterally administered to men or other animals. That is, in the case of injection, they can be directly dissolved in water or physiological saline solution, or further admixed with an antioxidant (sodium pyrosulfite, etc.), a paineasing agent (procaine hydrochloride, etc.), a preserving agent (methyl paraoxybenzoate, propyl paraoxybenzoate, etc.), a pH-controlling agent (sodium hydroxide, etc.).

Furthermore, tetrocarcins and the salts can be administered in forms of powder, tablets, granules, capsules, suppository, suspension, emulsion, etc. as mixed with pharmaceutical adjuvants such as a diluent (for example, starch, sucrose, lactose, calcium carbonate, kaolin, etc.), an extender (for example, lactose, starch, calcium carbonate, calcium phosphate, kaolin, bentonite, talc, etc.), a lubricant (for example, stearic acid, paraffin, boric acid, silica, sodium benzoate, polyethylene glycol, etc.) and the like.

When tetrocarcins and the salts are used as an antipiroplasma agent, they are administered continuously or intermittently at a dosage of 0.1–20.0 mg/kg (particularly 0.32–9.6 mg/kg) as tetrocarcins once a day with 1–7 administrations as one treatment. They are administered generally by intravenous injection. Subcutaneous injection, intramuscular injection, intraperitoneal administration, and oral administration are also applicable.

When tetrocarcins and the salts are used as an antimalaria agent, they can be administered at a dosage of 0.5–10 mg/kg as tetrocarcins with the same number of administrations in the same manner as above.

Embodiment of the present invention will be described, referring to examples.

EXAMPLE 1

Blood was let from BR-infected mice, and diluted with physiological saline solution so that the number of protozoa might be $8.6 \times 10^5/0.2$ ml to obtain a liquid of the infected blood cells. The liquid was i.p. inoculated in mice of groups, each of which is consisting of 5 animals, to obtain infected mice.

Tetrocarcins A and B were subcutaneously injected to the mice once a day for a mouse for a continuation of 7 days just from the point in time when all the groups were injected. Dosages of tetrocarcin A were each 0.1 ml as the liquid given in Table 1, and that of tetrocarcin B was each 0.1 ml as the 0.1 mg/0.1 ml liquid.

Survival ratio of mice is shown in Table 1.

In the control group of non-administered 5 mice, one mouse died on the 7th day, and four mice on the 8th day, so that all mice died till that day. Remarkable anemia, distinct hypertrophy and anemia of liver, distinct hypertrophy of spleen, distinct hypertrophy of mesenteric lymph nodes were observed by autopsy, and sometimes remarkable jaundice was observed. Parasitism of BR was highly observed in red blood cells.

On the other hand, when tetrocarcin A was administered at a dosage of at least 0.025 mg/day/mouse and tetrocarcin B at a dosage of 0.1 mg/day/mouse for a continuation of 7 days from the day of BR infection, all the mice could survive for more than one month, and the tetrocarcins were found effective.

TABLE 1

| Tetrocarcin | Dosage (mg/0.1 ml) | Survival days |
|---|---|---|
| A | 0.0125 | 4 × 9 days, 1 × 10 days |
|  | 0.025 | 5 × >30 days |
|  | 0.05 | " |
|  | 0.1 | " |
|  | 0.2 | " |
|  | 0.4 | " |
| B | 0.1 | " |
| Control |  | 1 × 7 days, 4 × 8 days |

EXAMPLE 2

Infected mice obtained in the same manner as in Example 1 were used for test. Tetrocarcin A was administered at dosages shown in Table 2 with reduced number of subcutaneous administration to 1–5 times. The results are shown in Table 2.

Control group of non-administered 5 mice all died till the 9th day, and their autopsy observation and results of protozoa investigation were the same as those of the control group in Example 1.

TABLE 2

| Dosage (mg/0.1 ml) | Administration day | Survival days |
|---|---|---|
| 0.05 | 1 | 3 × 8 days, 2 × 10 days |
|  | 2 | 1 × 10 days, 2 × 11 days |
|  |  | 1 × 12 days, 1 × >30 days |
|  | 3 | 1 × 11 days, 1 × 13 days |
|  |  | 1 × 14 days, 2 × >30 days |
|  | 5 | 1 × 15 days, 1 × 16 days |
|  |  | 1 × 17 days, 1 × 19 days |
|  |  | 1 × >30 days |
| 0.1 | 2 | 2 × 14 days, 1 × 16 days |

TABLE 2-continued

| Dosage (mg/0.1 ml) | Administration day | Survival days |
|---|---|---|
| 0.2 | 3 | 2 × 30 days<br>5 × >30 days |
|  | 1 | 1 × 13 days, 1 × 14 days<br>1 × 15 days, 2 × >30 days |
|  | 2 | 5 × >30 days |
|  | 3 | " |
|  | 5 | " |
| 0.4 | 1 | " |
| 0.8 | 1 | " |
| Control |  | 4 × 8 days, 1 × 9 days |

EXAMPLE 3

Test was carried out in the same manner as in Example 1 with 0.1 ml for each administration and administration schedule as given in Table 3.

TABLE 3

| Group | Dosage (mg/0.1 ml) | Administration days |
|---|---|---|
| 1 | 0.4 | 0 |
| 2 |  | 2 |
| 3 |  | 4 |
| 4 |  | 6 |
| 5 | 0.2 | 0, 1 |
| 6 |  | 2, 3 |
| 7 |  | 4, 5 |
| 8 |  | 6, 7 |
| 9 | 0.1 | 0, 1, 2 |
| 10 |  | 2, 3, 4 |
| 11 |  | 4, 5, 6 |
| 12 |  | 6, 7, 8 |
| 13 | 0.05 | 0, 1, 2, 3, 4, 5, 6 |
| 14 | 0 | Control (A) |
| 15 | 0 | Control (B) |

*The day of infection is set to zero day.

Blood smearing test: Blood smearing samples were prepared from some mice in the course of infection to examine the existence of BR infection.

Challenge: In the groups survived for more than one month after the infection, some mice (for example, three in the groups of all 5 mice as survived) were intraperitoneally inoculated with the same number of BR as that at the first inoculation to conduct challenge.

Serum reaction: Mice survived after the challenge were killed together with the non-challenged, survived mice, more than one month after the challenge to recover blood plasma. Agar gel precipitation test reaction was carried out using the thus obtained blood plasma and blood plasma antigen collected during the peak period of parasitemia (parasitemia means a state that protozoa appear in red blood cells). The results are shown in Table 4.

TABLE 4

Comparison of short-term administration according to various administration schedules of tetrocarcin A on BR-inoculated mice

| Group No. | Administration Dosage, Number of administration | Schedule | Parasitemia Result (day of examination) | Dead mice Number | Dead mice Survival days | Number of survived mice | Challenge Number of mice | Challenge Number of dead mice | Challenge Number of survived mice | Agar gel precipitation test Unchallenge* | Agar gel precipitation test Challenge* | Effectivity A | Effectivity B |
|---|---|---|---|---|---|---|---|---|---|---|---|---|---|
| 1 | 0.4 mg | 0 day | −(6) | 0 |  | 5 | 3 | 3 | 0 |  |  | 5/5 | 3/3 |
| 2 | Once | 2 | −(6) | 0 |  | 5 | 3 | 1 | 2 | 2/2 | 0/2 | 5/5 | 1/3 |
| 3 |  | 4 | −(6) | 0 |  | 5 | 3 | 0 | 3 | 1/2 | 0/3 | 5/5 | 0/3 |
| 4 |  | 6 | +(6) | 3 | 7,8,9 | 2 | 1 | 0 | 1 | 0/1 | 0/1 | 2/5 | 0/3 |
| 5 | 0.2 mg | 0–1 | −(8) | 0 |  | 5 | 3 | 3 | 0 |  |  | 5/5 | 3/3 |
| 6 | Twice | 2–3 | −(8) | 0 |  | 5 | 3 | 2 | 1 | 2/2 | 0/1 | 5/5 | 2/3 |
| 7 |  | 4–5 | −(8) | 0 |  | 5 | 3 | 0 | 3 | 2/2 | 0/3 | 5/5 | 0/3 |
| 8 |  | 6–7 | +(6,8,9,10)<br>−(12,14) | 0 |  | 5 | 3 | 0 | 3 | 0/2 | 0/3 | 5/5 | 0/3 |
| 9 | 0.1 mg | 0–2 | −(8) | 2 | 15,17 | 3 | 1 | 1 | 0 |  |  | 3/5 | 1/1 |
| 10 | 3 times | 2–4 | −(8) | 2 | 16,18 | 3 | 2 | 0 | 2 | 0/1 | 0/2 | 3/5 | 0/2 |
| 11 |  | 4–6 | −(8) | 0 |  | 5 | 3 | 0 | 3 | 0/2 | 0/3 | 5/5 | 0/3 |
| 12 |  | 6–8 | +(6,8,9,10)<br>−(12,14) | 1 | 24 | 4 | 3 | 0 | 3 | 0/1 | 0/3 | 4/5 | 0/3 |
| 13 | 0.05 mg<br>7 times | 0–6 | −(3,6,8,12,14) | 0 |  | 5 | 3 | 1 | 2 | 2/2 | 0/2 | 5/5 | 1/3 |
| 14 | Infected non-administered |  | +(6),−(3) | 5 | 8,8,8,9,11 | 0 |  |  |  |  | 0/5 |  |  |
| 15 | Control |  | +(6) | 5 | 7,7,7,8,8 | 0 |  |  |  |  | 0/5 |  |  |

Remark
*Number of negative mice/number of examined mice
A: Number of survived mice/number of inoculated mice
B: Number of dead mice/number of challenged mice All the mice were survived after the initial infection by administration at 0 day, 2nd and 4th days with the once 0.4 mg administration group, by administration at 0–1st days, 2nd–3rd days, 4th–5th days and 6th–7th days with the twice 0.2 mg administration group, by administration at 4th–6th days with the three times, 0.1 mg administration group, and by administration at 0–6th days with the 7 times 0.05 mg administration group, and the tetrocarcins were found effective.

When the appearance of parasitemia examined in the course of infection, results of the challenge on the survived mice, results of agar gel precipitation test of serum at the final killing, etc. were overall taken into account, it were only the groups 1 and 5 in which the parasitemia was negative in the course of infection and all the mice died after the challenge infection, and it was found very effective to administer 0.4 mg once or 0.2 mg twice at the incipient period of infection.

EXAMPLE 4

Since tetrocarcins A and B were found very effective as a result of the test with BR parasitized to small animals, the former tetrocarcin A was investigated of the effectiveness and practicability on TS, using cattle.

Splenectomized cattle with weight of about 200 kg were infected with TS Fukushima strain subcutaneously by inoculation once with $1 \times 10^9$ cells to obtain TS-infected cattle.

Administration was all by intravenous injection with dosages of 0.32 mg/kg and 3.2 mg/kg for each cattle, twice or three times every day or every other day. TS parasitemia on red blood cells are shown in Table 5.

TABLE 5

| Number  | Parasitemia (%) |         |        |
|---------|-----------------|---------|--------|
| of days | 0.32 mg/kg      | 3.2 mg/kg       |
| −7      | 1.6             | 0.2     | 7.5    |
| −6      | /               | 1.4     | /      |
| −5      | /               | /       | 15.3   |
| −4      | 4.9             | 5.0     | /      |
| −3      | 10.5            | 5.7     | 19.1   |
| −2      | 22.2            | 13.5    | /      |
| −1      | 24.2            | 18.4    | 18.6   |
| 0       | •25.0           | •23.3   | •22.5  |
| 1       | •28.1           | /       | /      |
| 2       | •28.5           | 18.5    | •20.8  |
| 3       | 28.8            | 3.7     | 13.8   |
| 4       | /               | 6.9     | •8.2   |
| 5       | 30.4            | 4.4     | /      |
| 6       | /               | 4.4     | 3.0    |
| 7       | 27.8            | •3.5    | 1.9    |
| 8       | 18.0            | 0.8     | 0.1    |
| 9       | /               | 0.1     | 0.1    |
| 10      | 15.8            |         | 0      |
| 11      | 12.3            |         |        |
| 12      | 4.4             |         |        |
| 13      | 3.3             |         |        |
| 14      | 2.0             |         |        |
| 15      | 1.5             |         |        |
| 16      | 0.9             |         |        |
| 17      | 1.0             |         |        |
| 18      | 0.7             |         |        |
| 19      | 0.7             |         |        |
| 20      | 0.7             |         |        |

Mark •: Administration of tetrocarcin A,
/: not examined

As is exhibited in Table 5, in the case of 0.32 mg/kg/day/cattle, administration was made once a day for a continuation of three days, when the TS parasitemia exceeded 25%.

In the case of twice administration of 3.2 mg/kg/day/cattle, first administration was made when the parasitemia of TS exceeded 23%. Since the parasitemia was reduced to 3.5% on the 7th day of administration, further administration was made at the same dosage, and the parasitemia was considerably reduced to 0.1% on the 2nd day.

In the case of administration of 3.2 mg/kg/day/cattle three times every other day, the administration was started when the TS parasitemia exceeded 22.5%. The parasitemia was rapidly lowered to, for example, 0.1% on the 4th day after the last administration and 0% on the 6th day. It was thereby clarified that the tetrocarcin was effective.

EXAMPLE 5

TS-infected cattle were obtained in the same manner as in Example 4 to investigate the effectiveness of tetrocarcin A.

Tetrocarcin was intravenously administered at a dosage of 6.4 mg/kg/cattle 2-3 times every other day. The results are shown in Table 6.

TABLE 6

| Number  | Parasitemia (%) |        |
|---------|-----------------|--------|
| of days | 6.4 mg/kg       |        |
| −7      | 1.3             | 1.2    |
| −6      | 1.4             | 3.7    |
| −5      | /               | 4.9    |
| −4      | 4.6             | /      |
| −3      | 6.4             | 10.8   |
| −2      | 8.7             | 12.6   |
| −1      | 10.4            | 17.8   |
| 0       | •14.0           | •20.0  |
| 1       | 7.8             | 7.7    |
| 2       | •2.2            | •1.5   |
| 3       | 1.3             | 0.5    |
| 4       | /               | •0.6   |
| 5       | 1.0             | 0.1    |
| 6       | 0.45            | 0.05   |
| 7       | /               | 0      |
| 8       | 0               |        |

As is exhibited in Table 6, in the case of administration of 6.4 mg/kg/day/cattle twice every other day, the administration was started when the TS parasitemia exceeded 14%. The parasitic percentage was rapidly reduced to, for example, 1.0% on the 3rd day after the last administration, and 0% of the 6th day. Thus, the tetrocarcin was found effective.

In the case of administration of 6.4 mg/kg/day/cattle three times every other day, the administration was started when the TS parasitemia exceeded 20%. The parasitemia was lowered to 0.6% even on the last day of administration, 0.05% on the 2nd day after the last administration, and 0% on the 3rd day. Thus, the tetrocarcin was found to have a very strong anti-piroplasma action. The state of zero parasitemia was continued over 7 weeks thereafter, and a continued anti-piroplasma activity was also observed.

EXAMPLE 6

TS-infected cattle were obtained in the same manner as in Example 4 to conduct comparative tests on effect of tetrocarcin A, and a diminazene aceturate preparation (Ganasag) and an 8-aminoquionoline preparation (Pamaquine) as commercially available anti-piroplasma agents.

Tetrocarcin A was intravenously administered at a dosage of 6.4 mg/kg/cattle twice every other day, Ganasag was intramuscularly administered at a dosage of 10.0 mg/kg/cattle continuously for two days, and Pamaquine was subcutaneously injected at a dosage of 1.6 mg/kg/cattle continuously for two days.

The administration was made for each when the TS parasitemia of cattle exceeded 20%. It was found from the results that in the case of tetrocarcin A-administered cattle, the parasitemia was rapidly lowered to, for example, 1.5% on the 4th day and 0% on the 7th day, and that the tetrocarcin was effective.

On the other hand, in the case of Ganasag-administered cattle the parasitemia was reduced to 5% on the 6th day, but scarcely reduced thereafter, and, to the contrary, increased up to 15% on the 14th day. Thus, the effect was not recognized.

In the case of Pamaquine-administered cattle, the parasitemia was reduced to 10% on the 6th day, but scarcely reduced thereafter, and an increasing tendency was observed on the 14th day. Thus, the effect was not recognized.

EXAMPLE 7

TS-infected cattle were obtained in the same manner as in Example 4 to investigate the effect of tetrocarcin A at the subcutaneous injection.

Tetrocarcin A was administered at dosages of 3.2 mg/kg and 6.4 mg/kg twice every other day, and the administration was started when the TS parasitemia exceeded 25%.

In the case of administration of 3.2 mg/kg twice every other day, the parasitemia was reduced to 0.2% on the 7th day after the end of administration. Thus, the tetrocarcin was found effective.

In the case of administration of 6.2 mg/kg twice every other day, the parasitemia was reduced to 1.2% on the 3rd day after the end of administration, and 0% on the 6th day. The tetrocarcin was found effective as in the case of intravenous administration. No side effects such as induration, edema, pyrexia, etc. were observed at all at the administration.

EXAMPLE 8

Safety of cattles by administration of tetrocarcin A: By intravenous, subcutaneous, intramuscular, intraperitoneal and oral administrations of 0.32 mg/kg-20.0 mg/kg/cattle once a day continuously for 2-7 days, no side effects from clinical findings such as pyrexia, anorexia, nausea, pain, induration, edema, etc. and no side effects from blood inspection findings were observed at all.

EXAMPLE 9

Blood was let from *Plasmodium berghei* (which will be hereinafter referred to as PB)-infected mice and diluted with physiological saline so that the number of protozoa might be $2 \times 10^6/0.2$ ml to obtain a liquid of the infected blood cells. The liquid was i.p. inoculated in mice of groups, each of which is consisting of 5 animals, to obtain infected mice. Tetrocarcin A was subcutaneously injected into mice once a day for each mouse continuously for seven days from the time when all the groups were infected, and the course was observed. Tetrocarcin A was administered at dosages of 0.025, 0.05 and 0.1 mg/mouse/day.

As the result, in the control group of non-administered 5 mice, two mice died on the 7th day, 2 mice on the 8th day, and one mouse on the 9th day. That is, all mice died. At the autopsy, infected blood cells were found in all the mice.

On the other hand, in the case of administration of tetrocarcin A at 0.025 mg/mouse/day, one mouse died on the 8th day, two on the 10th day, and two on the 11th day even by continuous administration for 7 days. That is, all the mice died. No remarkable difference was observed from the control group of non-administration.

In the case of continuous administration for 7 days at 0.05 mg/mouse/day, one mouse died each on the 16th day, 19th day, 20th day and 25th day, but one mouse survived for more than 40 days. Thus, some effect was observed.

In the case of continuous administration for 7 days at 0.1 mg/mouse/day, no symptom of disease was observed at all on all the mice, and all the mice survived for more than 40 days. Thus, the tetrocarcin was found effective. Blood was let from this group of mice at their tail veins on the 15th day to inspect malaria protozoa, but it was found that all the mice were negative. The mice were killed on the 44th day, and no infected blood cells were observed on all the mice. Furthermore, no remarkable changes were observed even by autopsy, and no malaria protozoa was observed in the smearing samples of the liver, spleen, lung, kidney, heart, thymus and brain.

The said seven organs of 5 mice were pooled to make a suspension in physiological saline solution, and the suspension was i.p. inoculated into two mice as mice of the second generation. The two mice of second generation had no symptom of disease, and were killed on the 36th day after the inoculation. No remarkable changes were observed by autopsy, and no malaria protozoa was observed in the smearing samples of the liver, spleen, lung, kidney, heart, and thymus. Thus, the medicine was found effective.

EXAMPLE 10

Test was conducted with PB-infected mice obtained in the same manner as in Example 9.

Tetrocarcin A was administered at dosages of 0.1, 0.2 and 0.4 mg/mouse/day, once a day continuously for 7 days.

As the result, in the case of control group of non-administration, all the mice died till the 8th day, whereas in the case of administration of tetrocarcin A at a dosage of 0.1 mg/mouse/day or more, all the mice had no symptoms of disease and survived, and were killed on the 40th day. In the meantime, results of protozoa inspection at the 15th day and at the killing were found negative. Furthermore, the mice of the second generation, which was i.p. inoculated with an emulsion of the internal organs of the mice of the first generation at the killing, also survived without any symptom of disease, and were killed on the 40th day. The results of the protozoa inspection were negative, and the effect of medicine was recognized.

EXAMPLE 11

Test was conducted with mice of groups, each consisting of PB-infected 5 mice, obtained in the same manner as in Example 9.

Tetrocarcin B was subcutaneously administered at dosages of 0.1, 0.2 and 0.4 mg/mouse/day, once a day for a continuation of 7 days. As the result, the control group of non-administered 5 mice all died, and it was found by autopsy that infected blood cells were observed in all the mice.

On the other hand, in the case of administration of tetrocarcin B at 0.1 mg/mouse/day, prolongation of survival days was somewhat observed, but each mouse died on the 10th, 13th, 17th, 20th, and 23rd days. That is, all 5 mice died.

In the case of administration at 0.2 mg and 0.4 mg/mouse/day, mice survived without any symptom of disease, and were killed on the 40th day. Results of protozoa inspection at the 15th day and at the killing were negative, and mice of the second generation i.p. inoculated with an emulsion of organs of the killed mice of first generation also survived without any symptom of disease, and were killed on the 40th day. Results of protozoa inspection was negative, and the effect of medicine was recognized.

EXAMPLE 12

Test was carried out in the same manner as in Example 3. The results are shown in Table 7.

TABLE 7

| Drug[*1] | Dosage (mg/day) | Survival days | Survival days after challenge | Agar gel precipitation test[*2] Unchallenge | Agar gel precipitation test[*2] Challenge |
| --- | --- | --- | --- | --- | --- |
| A | 0.1 | 5 × 30 days | 1 × 8 days<br>1 × 9 days<br>1 × 10 days | 2/2 | — |
| B | 0.1 | 5 × 30 days | 1 × 8 days<br>2 × >11 days | 0/2 | 0/2 |
| C | 0.2 | 5 × 30 days | 1 × 9 days<br>1 × 10 days<br>1 × >11 days | — | — |

[*1] A, B and C: tetrocarcins A, B and C
[*2] Number of negative mice/number of examined mice Tetrocarcins B and C exhibited considerable effect, and all the BR-infected mice survived. In the result after the challenge in the tetrocarcin B-administered group, one of the challenged 3 mice died on the 8th day, but two mice survived. Agar gel precipitation test of the non-challenged two mice was positive. In the tetrocarcin C-administered group, two of the challenged 3 mice died on the 9th and 10th days, but one survived. Thus, the two drugs were found effective.

From the above results, it was clarified that both tetrocarcins B and C are effective on BR in a little dosage as in the case of tetrocarcin A, and it was suggested that the two drugs might be fully effective against Babesia and Theileria of cattle.

What is claimed is:

1. A method for treating piroplasma disease in mammals which comprises administering an effective amount of a pharmaceutical composition comprising at least one member selected from the group consisting of tetrocarcins A, B and C, alkali metals salts thereof, and alkaline earth metal salts thereof; and at least one pharmaceutical carrier useful for preparation of injection, powder, tablet, granular, capsule, suppository, suspension or emulsion.

2. A method according to claim 1 wherein the mammal is cattle.

3. A method according to claim 1 or 2 wherein the effective amount is a dosage of 0.1 to 20.0 mg/kg/day as tetrocarcins.

4. A method for treating malaria in mammals which comprises administering an effective amount of a pharmaceutical composition comprising at least one member selected from the group consisting of tetrocarcins A, B and C, alkali metal salts thereof, and alkaline earth metal salts thereof; and at least one pharmaceutical carrier useful for preparation of injection, powder, tablet, granular, capsule, suppository, suspension or emulsion.

5. A method according to claim 4 wherein the effective amount is a dosage of 0.5 to 10 mg/kg/day as tetrocarcins.

* * * * *